United States Patent [19]

Murayama et al.

[11] Patent Number: 5,000,926
[45] Date of Patent: Mar. 19, 1991

[54] CATALYST LAYER-FIXED REACTOR

[75] Inventors: Katsutoshi Murayama; Masaaki Kuwa, both of Niigata, Japan

[73] Assignees: Mitsubishi Gas Chemical Company Inc.; Mitsubishi Heavy Industries, Ltd., both of Tokyo, Japan

[21] Appl. No.: 248,903

[22] Filed: Sep. 23, 1988

[30] Foreign Application Priority Data

Sep. 25, 1987 [JP] Japan ................... 62-238790

[51] Int. Cl.$^5$ ............................... B01J 8/06
[52] U.S. Cl. .................... 422/197; 422/148; 422/198; 422/201; 423/360
[58] Field of Search ............ 422/148, 197, 198, 201; 423/360; 518/706, 712

[56] References Cited

U.S. PATENT DOCUMENTS 3,268,299 8/1966 Russell .................... 422/197

FOREIGN PATENT DOCUMENTS 1098288 3/1981 Canada .
2169218 7/1986 United Kingdom .

Primary Examiner—David L. Lacey
Assistant Examiner—William H. Beisner
Attorney, Agent, or Firm—Wenderoth, Lind & Ponack

[57] ABSTRACT

This invention provides a catalyst layer-fixed reactor for an exothermic reaction which comprises a plurality of reaction tubes disposed within a shell of the reactor, an inner tube disposed in the middle portion of each of the reaction tubes, catalyst layers formed by catalyst charged in the space inside the reaction tubes and outside the inner tubes, and a cooling medium charged between each of the reaction tubes and the shell, and in which a feed gas is flowed in each of the inner tubes in cocurrent to feed gas flowing in the fixed catalyst layer.

5 Claims, 1 Drawing Sheet

CATALYST LAYER-FIXED REACTOR

FIELD OF THE INVENTION

This invention relates to a reactor to carry out an exothermic reaction of a feed gas in a fixed catalyst layer thereof.

A catalyst layer-fixed reactor of this invention is used, for example, as a reactor to synthesize methanol from a feed gas containing hydrogen, carbon monoxide and/or carbonic acid gas, or as a reactor to synthesize ammonia from a feed gas containing hydrogen and nitrogen.

PRIOR ARTS OF THE INVENTION

In a catalyst layer-fixed reactor, in general, flowing gases are scarcely mixed with one another in the axial direction, and nearly form an extrusion flow. Therefore, high reaction yields can be obtained. Further, the catalyst layer-fixed reactor can be applied to a wide range of reactions of from high reaction rate to low reaction rate, since the contact time between a reaction gas flow and a catalyst can be varied in a wide range.

When the heat of reaction is not large or when a feed gas to be supplied to a reactor contains a large amount of inert gas, an adiabatic, catalyst layer-fixed reactor is generally used. In a reaction giving a comparatively high heat of reaction, the catalyst layer is separated into several beds of catalyst layers, and a feed gas having a low temperature is introduced between one layer and another. Or there is used a multilayer adiabatic reactor having heat-exchanger(s) between one layer and another to adjust the temperature of the reaction feed in the entrance to each layer.

In a reactor for high pressure gas, the heat transfer coefficient becomes large due to high pressure. Therefore, there is used a self-heat-exchange type reactor in which a feed gas is charged to a preheating tube provided within a catalyst layer to preheat the feed gas by the reaction heat, and at the same time the temperature in the catalyst layer is controlled.

In the case where the reaction heat is comparatively large, generally, there is also used a tubular reactor in which many reaction tubes having small tube diameters are provided, catalysts are charged in the tubes and a cooling medium is circulated outside the tubes to remove the reaction heat.

In general, activity of catalyst, concentration of reactants, reaction temperature, reaction pressure, etc., can be cited as factors to influence the progress of an exothermic reaction. With regard to the reaction pressure among the above factors, a low operational pressure tends to be selected for the purpose of reducing the energy unit for the product, and, naturally, such a reduction of pressure brings a decrease in the reaction rate. With regard to the other factors, the operational conditions therefor are so selected as to increase the reaction rate, in order to make the process effective and highly efficient.

In the light of these points, the above catalyst layer-fixed reactors are evaluated as follows.

In the multilayer adiabatic reactor, a feed gas at a low temperature is introduced or a heat-exchanger is installed to compensate the increase of temperature caused by the exothermic reaction, and therefore, accomplishment of a more uniform temperature distribution in the layer requires an increase in the number of the catalyst layer beds or circulation of a large amount of gas resulting from the reaction, in order to reduce the temperature increase caused by the reaction.

In the self-heat exchange type reactor, in the case when a low pressure is selected for the above reason, many heat transfer tubes are necessary since the heat transfer coefficient between feed gas and reacted gas is small. Hence, the reactor is complicated and the cost for manufacture thereof increases.

Further, in the multilayer adiabatic reactor and self-heat exchange type reactor, heat exchange is required between gas at the reactor outlet and a medium to be heated, in order to use the energy of the reaction heat from generated steam, etc. For this reason, it is difficult to effect thermal recovery at high level.

The tubular reactor is effective for recovery of reaction heat generated in the reactor. However, it has had a defect that it is difficult to partially control a reaction in the reaction tube since a cooling medium having a constant temperature is circulated outside the reaction tube.

In U.K. Patent Publication No. 2,169,218, the present applicants have proposed, in order to solve the defect of the tubular reactor, a double tube-type exothermic reactor in which the reaction tube is formed into a double tube—an outer tube and an inner tube—, catalyst is charged into the tubular space inside the outer tube and outside the inner tube, and feed gas is flowed in the inner tube in counter current to a reaction gas flowing in the catalyst layer. In the above double tube-type exothermic reactor, since heat exchange between reacted gas and feed gas having a low temperature is effected on the outlet side in the catalyst layer, the temperature on the outlet side in the catalyst layer is decreased and it is therefore possible to prevent the decrease in the reaction rate caused by an increase in a concentration of a reaction product. Thus, said double tube-type exothermic reactor is desirable. However, since reaction gas flowing through the catalyst layer is heat-exchanged with feed gas having a high temperature on the entrance side in the catalyst layer, the reaction gas is likely to have a temperature peak on the entrance side in the catalyst layer if the reaction is too exothermic. And this temperature peak may give an unfavorable effect on the catalyst which is weak at a high temperature.

It is necessary to recover heat generated in the exothermic reaction, at as high as possible a level, and utilize the recovered heat effectively in order to reduce production cost. For this purpose, the above double tube-type exothermic reactor has been proposed to solve the defect of conventional tube-type reactors. However, when conditions are selected so as to increase the reaction rate in order to make the efficiency of the reactor high, the reactor has a temperature peak in the entrance portion of the catalyst layer since a sudden and sharp reaction takes place there.

When the temperature peak goes to an extreme, formation of by-products increases, the catalyst is thermally damaged, and the temperature control is finally made difficult. Further, there is a risk of a runaway reaction being caused. For this reason, when the conditions for high reaction rate are selected, the circular gas flow rate is increased, the reaction tubes are made small in diameter and increased in number so that the heat transfer areas are increased. However, the above measures lead to an increase in gas-circulation driving force and an increase in cost of manufacture of the reactor.

SUMMARY OF THE INVENTION

It is an object of this invention to provide a catalyst layer-fixed reactor which gives an increased reaction rate and high operating efficiency.

It is an object of this invention to provide a catalyst-layer fixed reactor which makes it possible to prevent the generation of the temperature peak in the entrance portion of the catalyst layer.

It is another object of this invention to provide a catalyst layer-fixed reactor which makes it possible to prevent thermal damage of the catalyst and reduce the formation of the reaction by-products.

It is another object of this invention to provide a catalyst layer-fixed reactor which makes it possible to increase the diameters of the reaction tubes and decrease the number of the reaction tubes.

It is yet another object of this invention to provide a catalyst layer-fixed reactor which permits a reduction in the gas-circulation driving force and a reduction in the cost of manufacture of a reactor.

This invention provides a catalyst layer-fixed reactor for a exothermic reaction which comprises a plurality of reaction tubes disposed within a shell of the reactor, an inner tube disposed in the middle portion of each of said reaction tubes, catalyst layers formed by catalyst charged in the space inside the reaction tubes and outside the inner tubes, and a cooling medium charged between each of the reaction tubes and the shell, and in which a feed gas is flowed in each of the inner tubes in cocurrent to gas flowing in the fixed catalyst layer.

DETAILED DESCRIPTION OF THE INVENTION

Figure 1:
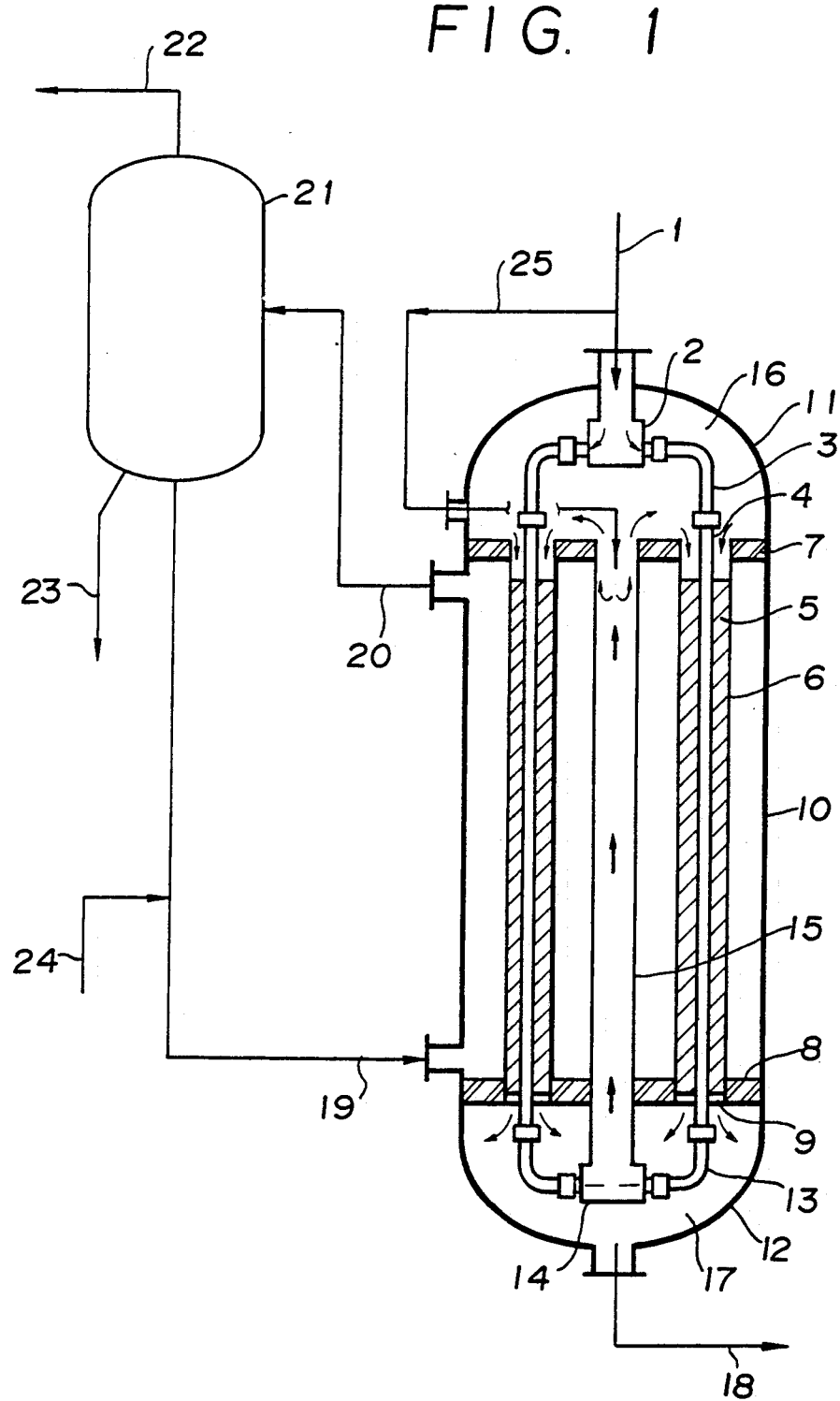
FIG. 1 shows a cross sectional view of the reactor of this invention.

A feed gas from the inner tube collects into one or a plurality of gas-collecting tubes and is supplied to the entrance portion of a catalyst layer. Part of the feed gas may be supplied to the gas-collecting tubes or into a channel chamber located on the gas entrance side of the catalyst layer without flowing it through the inner tube, to control the temperature in the entrance to the catalyst layer.

The inner diameter of a reaction tube suitably usable in the catalyst layer-fixed reactor of this invention is 50 to 150 mm, and the outer diameter of the inner tube is 1/5 to $\frac{1}{2}$ of the inner diameter of the reaction tube. In the case where the inner diameter of the reaction tube is less than 50 mm, the space between the reaction tube and the inner tube becomes narrow, and the particle size of the catalyst has to be made small. Hence, the pressure difference increases at gas flowing. When said inner diameter exceeds 150 mm, the surface area for heat transfer becomes insufficient as compared with the contents. Hence, it is made difficult to control the temperature in the catalyst layer. When the inner diameter of the reaction tube is in the above-specified range, if the outer diameter of the inner tube is less than 1/5 of the inner diameter of the reaction tube, the inner tube is too small as compared with the inner diameter of the reaction tube and therefore, the effect to be obtained by flowing feed gas in cocurrent flow to reaction gas flowing through the catalyst layer becomes small. Thus, the temperature peak in the entrance portion of the catalyst layer is not improved. And, if the outer diameter of the inner tube exceeds $\frac{1}{2}$ of the inner diameter of the reaction tube, the amount of catalyst charged inside the reaction tube and outside the inner tube is made small, and as a result, the number of necessary reaction tubes has to be increased. Further, since the space formed between the inner wall of the reaction tube and the outer wall of the inner tube becomes small, the diameter of catalyst is required to be decreased in order to charge the catalyst suitably, and there is an undesirable influence that the pressure loss in the catalyst layer increases.

In the case of synthesizing methanol from feed gas by using the catalyst layer-fixed reactor of this invention, generally, the catalyst used therefor is of a copper type, the reaction pressure is 40 to 200 kg/cm$^2$G and the reaction temperature is 200 to 300° C.

This invention will be explained hereinbelow according to the drawings. FIG. 1 shows one embodiment of the catalyst layer-fixed reactor according to this invention.

As the cooling medium in the catalyst layer-fixed reactor of this invention, not only saturated pressurized water but also oils, molten salts, etc., may be used. The following explanation is based on the use of saturated pressurized water, which is most generally used, as the cooling medium.

A feed gas is introduced through a gas supply tube 1, and supplied to an upper branch tube 3 through a gas distributor 2. Then, the gas is introduced into an inner tube 4 to cool a catalyst layer 5 charged in the space within the reaction tube 6 and outside the inner tube 4. The catalyst is supported by a supporting pan 9 provided in the lower end of the reaction tube 6. The reaction tube 6 is fixed with upper and lower tube sheets 7 and 8, and the tube sheets 7 and 8 are fixed with a shell 10 and upper and lower channel bonnets 11 and 12. Gas flowing through the inner tube 4 is heated through the tube wall and when it comes to the outlet of the inner tube, its temperature becomes nearly the same as that of the cooling medium.

Gas from the inner tube 4 is introduced through a lower branch tube 13 into a gas collector 14 and then to a gas collecting tube 15. The gas collecting tube 15 may be installed outside the reactor. Gas coming out of the gas collecting tube 15 is turned reversely, distributed equally into a plurality of reaction tubes 6 and introduced into the catalyst layer 5 to carry out the reaction.

Gas flowing through the catalyst is cooled by feed gas flowing in the inner tube 4 in cocurrent flow thereto and the cooling medium existent outside the reaction tube 6 collects in a lower channel chamber 17 and goes out of a tube 18.

On the other hand, the cooling medium (saturated pressurized water) is introduced through a tube 19 to the inside of the shell 10 of the reactor. The saturated pressurized water absorbs the reaction heat and part of it is evaporated and introduced into a gas-liquid separator 21 through a tube 20. Generated steam is extracted through a tube 22. A part of the saturated pressurized water is extracted through a tube 23 in order to prevent concentration of impurities. However, a major part of the saturated pressurized water is circulated through the tube 19. Saturated pressurized water is also replenished through a tube 24.

A part of feed gas may be introduced through a tube 25 into the gas collecting tube 15 to adjust the temperature at the entrance to the catalyst layer and make it possible to control the reaction rate.

EXAMPLES

Several reactors having different sizes of reaction tubes and inner tubes were used to ascertain the performance of the catalyst layer-fixed reactor according to this invention in reaction for synthesis of methanol. Further, reactions were also carried out under the same conditions by using conventional tubular reactors having different reaction tube diameters for comparison.

The reaction for synthesis of methanol was carried out by using a copper-type catalyst and under a pressure of 70 kg/cm$^2$G at a space velocity of 8,000 l/hr. The feed gas used had the following composition.

$CO_2$ = 5.3 vol.%
$CH_{14}$ = 9.1 vol.%
$CO$ = 10.9 vol.%
$N_2$ = 0.4 vol.%
$H_2$ = 74.0 vol.%
$CH_3OH$ = 0.3 vol.%

The reactor used had a structure as shown in FIG. 1, and the temperature of the catalyst layer was controlled by introducing a part of the feed gas into the gas collecting tube. The reaction tubes had a length of 15 m, and saturated pressurized water was used as a cooling medium. The temperature of the cooling medium was controlled by controlling the pressure of generated steam.

Table 1 shows the results of examples using the catalyst layer-fixed reactors and the results of Comparative Examples using tubular reactors. In Table 1, the gas temperature in entrance to the catalyst layer stands for a temperature of gas which was about to enter the catalyst layer, and the gas temperature in outlet from catalyst layer stands for a temperature of gas which has just passed the catalyst layer.

dium is 230° C., the highest temperature in the catalyst layer in Example 1 decreased by 30° C. (=284−254), and therefore, the reactors of this invention are advantageous in that the damage of catalyst and the formation of by-products should be prevented.

Further, the reactor of this invention makes it possible to increase the temperature of the saturated pressurized water without increasing the temperature of the catalyst layer so much. For example, in comparison (Examples 1 to 3) in reactors using reaction tubes having an inner diameter of 75 mm where the temperatures of cooling media were changed, it was possible to increase the temperature of the saturated pressurized water (cooling medium) by 10° C. from 230° C. to 240° C. by decreasing the temperature of feed gas to be supplied to the inner tube, whereby making it possible to increase the pressure of generated steam from 28.5 atm to 34.1 atm.

Further, in this invention, when a reactor having a proper ratio of the inner diameter of reaction tube to the outer diameter of inner tube is used and when it is operated by decreasing the temperature of feed gas to be supplied thereto, it is possible to decrease the number of reaction tubes remarkably since the size of the reaction tubes can be made large. For example, in Example 7 where the inner diameter of the reaction tube was 150 mm, the ratio of the inner diameter of the reaction tube to the outer diameter of the inner tube was 1:0.5 and the temperature of feed gas to be introduced into the reactor was 50° C., it was possible to obtain the gas temperature, in the catalyst layer, equal to that in Example 1. In contrast, the results of Comparative Examples 1 to 3 show that it was necessary to decrease the inner diameters of reaction tubes down to 40 mm, in order to obtain the gas temperature, in the catalyst layer, equal to those

TABLE 1

| | Inner diameter of reaction tube (mm) | Outer diameter of inner tube (mm) | Temperature of cooling medium (°C.) | Temperature of gas to be supplied to inner tube (°C.) | Gas temperature in catalyst layer | | | |
|---|---|---|---|---|---|---|---|---|
| | | | | | Entrance (°C.) | Outlet (°C.) | Highest (°C.) | Average (°C.) |
| Example | | | | | | | | |
| 1 | 75 | 20 | 230 | 150 | 230 | 236 | 254 | 243 |
| 2 | 75 | 20 | 240 | 100 | 240 | 243 | 263 | 250 |
| 3 | 75 | 20 | 240 | 50 | 240 | 244 | 255 | 247 |
| 4 | 150 | 38 | 230 | 50 | 230 | 235 | 274 | 247 |
| 5 | 150 | 38 | 230 | 150 | 230 | 239 | 292 | 255 |
| 6 | 150 | 50 | 230 | 50 | 230 | 237 | 263 | 245 |
| 7 | 150 | 75 | 230 | 50 | 230 | 240 | 253 | 240 |
| 8 | 150 | 75 | 230 | 150 | 230 | 237 | 278 | 250 |
| Comparative Example | | | | | | | | |
| 1 | 40 | | 230 | | 230 | 234 | 253 | 240 |
| 2 | 50 | | 230 | | 230 | 234 | 263 | 243 |
| 3 | 75 | | 230 | | 230 | 235 | 284 | 249 |

It is seen from these results that in the reactor of this invention, the temperature in the catalyst layer is uniformly distributed as compared with the conventional tubular reactor. To compare the reactors of these two types, for example, in the case where the inner diameters of the reaction tubes are 75 mm, the differences between the highest temperature and the average temperature in the catalyst layer are 8 to 13° C. in Examples 1 to 3 of this invention. Meanwhile, said difference is 35° C. in Comparative Example 3 of the tubular reactor. That is, said differences in the reactors of this invention are about ¼ to ⅓ of that in the conventional tubular reactor.

In a comparison between Example 1 and Comparative Example 3 where the temperature of cooling mein Examples 1 and 7.

To compare the number of reaction tubes on the basis of the cross sectional area of catalyst layer, the ratio of the number of reaction tubes having an inner diameter 75 mm in Example 1 to the number of reaction tubes having an inner diameter of 40 mm in the conventional tubular reactor is 1:3.3, and the ratio of the number of reaction tubes having an inner diameter of 150 mm in Example 7 to the number of those mentioned above is 1:10.5. As is seen here, the reactor of this invention makes it possible to decrease the number of reaction tubes to less than about ⅓ of those to be used in the conventional tubular reactor.

In the catalyst layer-fixed reactor of this invention, heat is continuously removed from the entrance zone to the catalyst layer where the reaction proceeds at rapid rates, by providing an inner tube in the middle portion of a catalyst reaction tube and flowing a feed gas in the inner tube in cocurrent flow to gas flowing in the catalyst layer. Therefore, the temperature in the catalyst layer is made even and the temperature increase occurring suddenly and sharply in the entrance portion to the catalyst layer is moderated. Thus, the following effects are produced.

(1) Since the temperature peak is moderated to a great extent, the thermal damage both to catalyst and the interior of a reactor is prevented. The highest temperature in catalyst is also decreased, and therefore, the formation of by-products is decreased. For the above reasons, the life of catalyst is improved, and the procedure of purification of the reaction product is made easy.

(2) Since the temperature peak is moderated, it is made possible to increase the temperature of cooling medium. When the cooling medium is saturated pressurized water, steam having higher pressure is recovered. Therefore, in a plant where a steam turbine using the above generated steam can be used, the total heat efficiency becomes high and the energy unit is improved.

(3) As compared with conventional tubular reactors, it is possible to make the diameters of reaction tubes large, and the number of reaction tubes can be decreased to less than about ⅓. Further, since the temperature peak is moderated, the concentration of effective components in feed gas may be high. Therefore, the amount of gas for circulation can be decreased. Since the number of reaction tubes is reduced, it is made easier to design the alignment of reaction tubes suitably, and there is an effect that the column diameter of the reactor can be made small.

For these reasons, the reactor of this invention makes it possible to reduce the cost of manufacture thereof, and makes it easy to manufacture the same in a large size.

What we claim is:

1. A catalyst layer-fixed reactor for an exothermic reaction which comprises a plurality of reaction tube means disposed within a shell means, a first end of said reaction tube means being in flow communication with a first gas reactant inlet means and a second end of said reaction tube means being in flow communication with a gas exit means, said shell means having cooling medium inlet means and cooling medium outlet means positioned on said shell means for delivering a cooling medium flow therein to cool the gas in said reaction tube means, inner tube means disposed individually within said reaction tube means, catalyst layers individually packed in spaces inside said reaction tube means and outside said inner tube means, a first end of said inner tube means being adjacent to said first end of said reaction tube means and being in flow communication with a second gas reactant inlet means, a second end of said inner tube means being adjacent to said second end of said reaction tube means, a gas collecting tube means being positioned so as to provide flow communication between said second end of said inner tube means and said first gas reactant inlet means, so that an exothermic reaction is carried out by allowing a feed gas to flow in the inner tube means in cocurrent flow to a gas flowing in the catalyst layers after the gas has passed the inner tube means and the collecting tube means.

2. A catalyst layer-fixed reactor according to claim 1, wherein said first gas reactant inlet means and said gas exit means are defined by channel bonnets and tube sheets.

3. A catalyst layer-fixed reactor according to claim 1, wherein said second gas reactant inlet means comprises a tube header in flow communication with a feed gas supply tube.

4. A catalyst layer-fixed reactor according to claim 3, wherein said feed gas supply tube is also in flow communication with said first gas reactant inlet means.

5. A catalyst layer-fixed reactor according to claim 1, wherein an inner diameter of said reaction tube means is 50 to 150 mm and an outer diameter of said reaction tube means is 1/5 to ½ of the inner diameter of said reaction tube means.

* * * * *